(12) United States Patent
White

(10) Patent No.: US 7,279,606 B1
(45) Date of Patent: Oct. 9, 2007

(54) HYDROFORMYLATION PROCESS

(75) Inventor: Daniel F. White, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/731,994

(22) Filed: Apr. 2, 2007

(51) Int. Cl.
*C07C 45/50* (2006.01)
*C07C 31/18* (2006.01)

(52) U.S. Cl. .................... 568/454; 568/852; 568/862
(58) Field of Classification Search ............... None
See application file for complete search history.

(56) References Cited

U.S. PATENT DOCUMENTS

| | | | |
|---|---|---|---|
| 4,064,145 A | 12/1977 | Taylor | 260/346.11 |
| 4,215,077 A | 7/1980 | Matsumoto et al. | 568/454 |
| 4,238,419 A | 12/1980 | Matsumoto et al. | 568/454 |
| 4,306,087 A | 12/1981 | Matsumoto et al. | 568/454 |
| 4,567,305 A | 1/1986 | Matsumoto et al. | 568/454 |
| 4,678,587 A | 7/1987 | Voinche et al. | 210/748 |
| 5,290,743 A | 3/1994 | Chang | 502/30 |
| 5,504,261 A | 4/1996 | Mullin et al. | 568/862 |
| 6,127,584 A | 10/2000 | Zajacek et al. | 568/852 |
| 6,225,509 B1 | 5/2001 | Dubner et al. | 568/454 |
| 6,426,437 B1 * | 7/2002 | Shum | 568/862 |

FOREIGN PATENT DOCUMENTS

| | | |
|---|---|---|
| JP | 06-279344 | 10/1994 |
| JP | 06-279345 | 10/1994 |

* cited by examiner

*Primary Examiner*—Sikarl A. Witherspoon
(74) *Attorney, Agent, or Firm*—Kevin M. Carroll

(57) ABSTRACT

A process for the production of 4-hydroxybutyraldehyde is described. The process comprises reacting allyl alcohol with a mixture of carbon monoxide and hydrogen in the presence of a solvent and a catalyst system comprising a rhodium complex and a trans-1,2-bis(bis(3,5-di-n-alkylphenyl)phosphinomethyl)-cyclobutane. The process gives high yield of 4-hydroxybutyraldehyde compared to 3-hydroxy-2-methylpropionaldehyde.

11 Claims, No Drawings

HYDROFORMYLATION PROCESS

FIELD OF THE INVENTION

This invention relates to a process for hydroformylating allyl alcohol to produce 4-hydroxybutyraldehyde. The process produces an unexpectedly high ratio of 4-hydroxybutyraldehyde:3-hydroxy-2-methylpropionaldehyde (linear:branched) product.

BACKGROUND OF THE INVENTION

The hydroformylation of allyl alcohol is a well-known and commercially practiced process. See, for example, U.S. Pat. Nos. 4,064,145, 4,215,077, 4,238,419, 4,678,857, and 5,290,743. In the hydroformylation reaction, allyl alcohol is reacted with a $CO/H_2$ gas mixture in the presence of a catalyst to form 4-hydroxybutyraldehyde (HBA). The HBA may then be separated from the catalyst, e.g., by water extraction, and hydrogenated to form 1,4-butanediol (BDO). See U.S. Pat. No. 5,504,261.

Various catalyst systems have been employed for the hydroformylation reaction, most notably a rhodium complex together with a phosphine ligand (see, e.g., U.S. Pat. Nos. 4,064,145, 4,238,419, and 4,567,305). Commonly employed phosphine ligands are trisubstituted phosphines such as triphenyl phosphine. One disadvantage of the hydroformylation process is that other co-products or byproducts are also formed in addition to the desired HBA linear product. The hydroformylation of allyl alcohol typically produces some 3-hydroxy-2-methylpropionaldehyde (HMPA) branched co-product and $C_3$ byproducts such as n-propanol and propionaldehyde. Although HMPA may be hydrogenated to produce 1,3-methyl propanediol (MPD), which is a useful material, the MPD co-product reduces the yield of BDO. Formation of the $C_3$ byproducts effectively represents another yield loss in the process which can have a severe adverse effect on the process economics.

To increase BDO yields, research continues to improve the hydroformylation process and reduce less desired co-product/byproducts. U.S. Pat. No. 6,127,584 discloses that the use of a trialkyl phosphine ligand having at least 2 methyl groups results in increased HBA:HMPA ratio. The use of disphosphine ligands has also been found to improve the HBA:HMPA ratio. The hydroformylation of allyl alcohol using rhodium complex catalysts and disphosphine ligands such as DIOP or trans-1,2-bis(diphenyl-phosphinomethyl) cyclobutane is shown in the art, notably in Japan Kokai Nos. 06-279345 and 06-279344 and U.S. Pat. No. 4,306,087. U.S. Pat. No. 6,225,509 discloses that maintaining the concentration of CO in the reaction liquid above about 4.5 mmols/liter reduces the make of undesirable $C_3$ co-products when using a catalyst comprised of a rhodium complex and a ligand such as DIOP. In addition, co-pending U.S. patent application Ser. No. 11/580,510 discloses that using a 2,3-O-isopropylidene-2,3-dihydroxy-1,4-bis[bis(3,5-di-n-alkylphenyl)phosphino]butane ligand results in a very high yield of 4-hydroxybutyraldehyde compared to 3-hydroxy-2-methylpropionaldehyde.

In sum, new processes for hydroformylating allyl alcohol to produce 4-hydroxybutyraldehyde are needed. Particularly valuable processes would result in high ratios of 4-hydroxybutyraldehyde (HBA) compared to 3-hydroxy-2-methylpropionaldehyde (HMPA).

SUMMARY OF THE INVENTION

The invention is a process that comprises reacting allyl alcohol with carbon monoxide and hydrogen in the presence of a solvent and a catalyst system to produce 4-hydroxybutyraldehyde. The catalyst system comprises a rhodium complex and a trans-1,2-bis(bis(3,5-di-n-alkylphenyl)phosphinomethyl)-cyclobutane. The invention surprisingly results in high ratios of 4-hydroxybutyraldehyde product compared to 3-hydroxy-2-methylpropionaldehyde.

DETAILED DESCRIPTION OF THE INVENTION

The process of the invention comprises hydroformylating allyl alcohol in the presence of a solvent and a catalyst system. The catalyst system of the invention comprises a rhodium complex and a trans-1,2-bis(bis(3,5-di-n-alkylphenyl)phosphinomethyl)cyclobutane. Trans-1,2-bis(bis(3,5-di-n-alkyl-phenyl)phosphinomethyl)cyclobutane has the chemical formula:

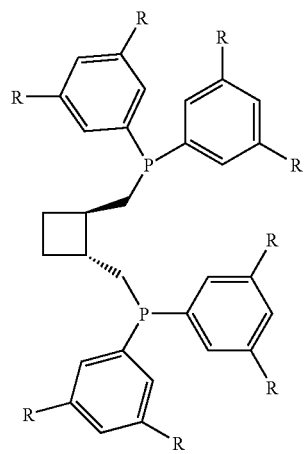

wherein R is an n-alkyl group. Preferably, R is methyl, ethyl, or propyl.

The disphosphine ligand is most preferably trans-1,2-bis (bis(3,5-dimethylphenyl)phosphinomethyl)cyclobutane or trans-1,2-bis(bis(3,5-diethyl-phenyl)phosphinomethyl)cyclobutane.

The trans-1,2-bis(bis(3,5-di-n-alkylphenyl)phosphinomethyl)cyclobutane may be prepared by any possible method. For instance, it may be prepared by the reaction of trans-1, 2-cyclobutanedimethanol, bis(toluenesulfonate) with lithium di(3,5-di-n-alkylphenyl)phosphine.

The catalyst system of the invention also comprises a rhodium complex. Suitable rhodium complexes contain rhodium attached to ligand groups. The rhodium complex is preferably soluble in the solvent. There are no particular restrictions regarding the choice of ligands attached to the rhodium complex. For example, suitable ligands include hydrides, carbonyl, substituted and unsubstituted cyclopentadienyls, 2,4-alkanedionates, trialkyl or triaryl phosphines, diphosphines, and mixtures thereof. Particularly preferred ligands include carbonyl, acetylacetonate (2,4-pentanedionate), triphenylphosphine, and mixtures thereof. Examples of preferred rhodium complexes include (acetylacetonato) dicarbonylrhodium and tris(triphenylphosphine)rhodium carbonyl hydride.

The rhodium complex can be pre-associated with the trans-1,2-bis(bis(3,5-di-n-alkylphenyl)phosphinomethyl)-cyclobutane prior to use in the hydroformylation reaction such that the bis(bis(3,5-di-n-alkylphenyl)-phosphinomethyl)-cyclobutane ligand forms part of the rhodium complex, or it can be added separately. However, it is preferable to add the rhodium complex separate from the trans-1,2-bis(bis(3,5-di-n-alkylphenyl)phosphinomethyl)-cyclobutane. The molar ratio of the trans-1,2-bis(bis(3,5-di-n-alkylphenyl)-phosphinomethyl)cyclobutane:rhodium complex is preferably in the range of 0.5:1 to 5:1.

Although not necessary, the catalyst system may additionally comprise a monophosphine compound. The monophosphine compound is in addition to any phosphine ligand that may be associated with the rhodium complex. The monophosphine compound is a trisubstituted phosphine that is represented by the formula:

$$(R^1)_3P$$

wherein $R^1$ is an aryl or alkyl group. Suitable aliphatic $R^1$ groups include methyl, ethyl, n-butyl, sec-butyl, octyl, and decyl. Suitable aromatic $R^1$ groups include phenyl, tolyl, and naphthyl. The $R^1$ groups may be the same or are different, but preferably are the same. Preferably, the monophosphine is a trisubstituted aryl phosphine. More preferably, the monophosphine is triphenylphosphine or tritolylphosphine. Triphenyl phosphine is particularly preferred.

A reaction solvent is also required for the process of the invention. Typical solvents are those that are capable of solubilizing the rhodium complex and are not reactive to the hydroxyaldehydes that are produced in the hydroformylation step. Suitable solvents include any organic solvent having very low or minimal solubility in water. Preferred solvents include $C_5$-$C_{20}$ aliphatic hydrocarbons, $C_6$-$C_{20}$ aromatic hydrocarbons, alcohols, ethers, and mixtures thereof. Particularly preferred solvents include toluene, cyclohexane, methyl t-butyl ether, and mixtures thereof.

Typical reaction conditions for the hydroformylation step are mild to favor the formation of the linear 4-hydroxybutyraldehyde (HBA) rather than branched 3-hydroxy-2-methylpropionaldehyde (HMPA) reaction product. Reaction conditions are preferably in the range of from about 20 to 120° C. and pressures of from about 20 to 600 psig, more preferably from about 45 to 85° C. and 30 to 400 psig, and most preferably from about 50 to 80° C. and 40 to 300 psig. The molar ratio of $CO:H_2$ is typically about 1:1, although the ratio can vary considerably. The partial pressure of CO is typically within the range of 5 to 100 psig. The partial pressure of hydrogen is typically within the range of 40 to 200 psig. The reaction is conducted at these conditions until a predominance of the allyl alcohol has reacted, e.g. 60 to 99.9%, the products being largely 4-hydroxybutyraldehyde with some branched reaction products. The amount of reaction time is not critical, but usually a reaction time of 0.5 to 4 hours is adequate.

Preferably, the allyl alcohol starting concentration on a reaction solvent to feed basis is in the range of about 5 to 40 percent by weight in the solvent; more preferably, lower concentration in the range of 5 to 10 percent by weight may be used.

Preferably, the hydroformylation of allyl alcohol is carried out such that the concentration of CO in the liquid phase ($[CO]_{liq}$) is maintained above 4 mmols/liter (0.004 M) during the hydroformylation. The value of $[CO]_{liq}$ is defined in U.S. Pat. No. 6,225,509, the teachings of which are incorporated herein by reference. Preferably, the liquid phase hydrogen:carbon monoxide molar ratio is in the range of from 10:1 to about 1:2, more preferably from 5:1 to about 1:2.

Following the hydroformylation step, the HBA product is preferably separated from the solvent and catalyst system by water extraction in an extraction vessel. Water extraction methods are well known in the art and can be affected by any suitable means, such as mixer-settlers, packed or trayed extraction columns, rotating disk contactors, or passed to a settling tank for resolution of the mixture into aqueous and organic phases. HBA, and any HMPA, remain soluble in the water (aqueous) phase and is separated from the solvent (organic) phase.

The 4-hydroxybutyraldehyde (and any 3-hydroxy-2-methylpropion-aldehyde) reaction product is preferably subjected to an additional step of hydrogenating the 4-hydroxybutyraldehyde in the presence of a hydrogenation catalyst to produce 1,4-butanediol (BDO). Hydrogen is added to the reaction vessel for the hydrogenation. Suitable hydrogenation catalysts include any Group VIII metal, such as nickel, cobalt, ruthenium, platinum, and palladium, as well as copper, zinc and chromium and mixtures and alloys thereof. Especially preferred are nickel catalysts. Most preferred are Raney®-type nickel and fixed bed nickel catalysts.

The hydrogenation reaction conditions are preferably in the range of from about 60 to 200° C. and pressures of from about 200 to 1000 psig, more preferably from about 80 to 140° C. and 300 to 1000 psig. Generally reaction times of 1 to 10 hours are appropriate. During the hydrogenation reaction, BDO and MPD formed while the high ratio of linear to branched products is substantially retained, along with other low co-product/byproducts.

The following examples merely illustrate the invention. Those skilled in the art will recognize many variations that are within the spirit of the invention and scope of the claims.

EXAMPLE 1

Preparation of Diphosphines 1A, 1B, and 1C: Diphosphines 1A, 1B, and 1C of the following general formula are prepared as described below.

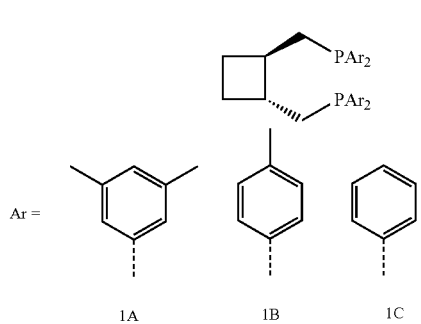

A solution of trans-1,2-cyclobutanedimethanol, bis(toluenesulfonate) in dry/degassed THF (1 equivalent, 1.73 g, 3.7×10$^{-3}$ moles of the dioxolane in 50 mL THF) is added drop-wise under argon to a solution of the appropriate lithium diarylphosphine (see formulae above) in dry/degassed THF (2.3 equivalents in 100 mL THF). The mixture is heated at reflux for 2 hours, then cooled, and the solvent is removed under reduced pressure. The remaining solids are re-dissolved in dichloromethane, filtered though a silica bed, and the solvent is removed under reduced pressure to yield the trans-1,2-bis(diarylphosphinomethyl)cyclobutane.

Diphosphine 1A: trans-1,2-bis(bis(3,5-dimethylphenyl)phosphinomethyl)cyclobutane.

Comparative Diphosphine 1B: trans-1,2-bis(bis(4-methylphenyl)phosphinomethyl)cyclobutane.

Comparative Diphosphine 1C: trans-1,2-bis(diphenylphosphinomethyl)cyclobutane.

1D, 1E, and 1F: Diphosphines 1D, 1E, and 1F of the following general formula are prepared as described below.

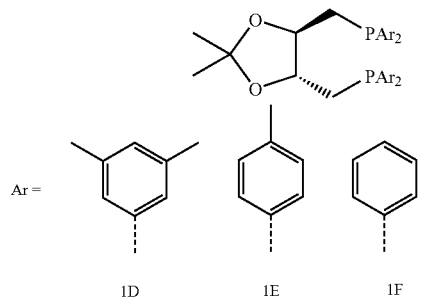

1D  1E  1F

A solution of 2,2-dimethyl-4,5-bis[(toluenesulfonyloxymethyl)methyl]-1,3-dioxolane in dry/degassed THF (1 equivalent, 1.73 g, $3.7 \times 10^{-3}$ moles of the dioxolane in 50 mL THF) is added drop-wise under argon to a solution of the appropriate lithium diarylphosphine (see formulae above) in dry/degassed THF (2.3 equivalents in 100 mL THF). The mixture is heated at reflux for 2 hours, then cooled, and the solvent is removed under reduced pressure. The remaining solids are re-dissolved in dichloromethane, filtered though a silica bed, and the solvent is removed under reduced pressure to yield the 2,3-O-isopropylidene-2,3-dihydroxy-1,4-bis(diarylphosphino)butane.

Comparative Diphosphine 1D: 2,3-O-isopropylidene-2,3-dihydroxy-1,4-bis[bis(3,5-dimethylphenyl)phosphino]butane.

Comparative Diphosphine 1E: 2,3-O-isopropylidene-2,3-dihydroxy-1,4-bis[bis(4-methylphenyl)phosphino]butane.

Comparative Diphosphine 1F: 2,3-O-isopropylidene-2,3-dihydroxy-1,4-bis[bis(phenyl)phosphino], known as DIOP.

EXAMPLE 2

Hydroformylation Reaction using Diphosphines

Allyl alcohol is hydroformylated using diphosphines 1A-1F according to the following procedure:

A solution of the desired diphosphine (2 equivalents or $8.6 \times 10^{-5}$ moles) in dry degassed toluene (15 g) is added to [Rh(CO)$_2$(acac)] (1 equivalent or $4.3 \times 10^5$ moles) in a 100 mL Parr autoclave. The solution is flushed three times with a 1:1 CO/H$_2$ mixture and then pressurized to 180 psig with the CO/H$_2$ mixture. The autoclave is then heated to 65° C. with stirring, allyl alcohol (3.5 mL) is injected, and the autoclave is pressurized to 200 psig with the CO/H$_2$ mixture. The autoclave is kept at a constant pressure of 200 psig, and the gas uptake of the reaction is monitored. When there is no further gas uptake, the autoclave is cooled and depressurized. The resulting solution is analyzed by gas chromatography to determine the products of the reaction. The reaction produces HBA, HMPA, and C$_3$ products (n-propanol and propionaldehyde).

The results, shown in Table 1, demonstrate that the trans-1,2-bis(bis(3,5-di-n-alkylphenyl)phosphinomethyl)cyclobutanes of the current invention unexpectedly result in significantly higher HBA:HMPA (l:b) ratio than any other comparable diphosphine.

TABLE 1

Diphosphine Comparisons

| Diphosphine | Conversion (%) | HBA (%) | HMPA (%) | C$_3$ (%) | l:b ratio |
|---|---|---|---|---|---|
| 1A | 99.50 | 91.0 | 8.3 | 0.2 | 11.0 |
| 1B* | 99.30 | 89.3 | 9.8 | 0.2 | 9.1 |
| 1C* | 99.94 | 88.6 | 10.8 | 0.1 | 8.2 |
| 1D* | 99.66 | 89.8 | 9.4 | 0.2 | 9.5 |
| 1E* | 99.98 | 86.5 | 11.3 | 0.2 | 7.7 |
| 1F* | 99.75 | 86.2 | 11.7 | 0.2 | 7.4 |

*Comparative Example

I claim:

1. A process to produce 4-hydroxybutyraldehyde comprising reacting allyl alcohol with carbon monoxide and hydrogen in the presence of a solvent and a catalyst system comprising a rhodium complex and a trans-1,2-bis(bis(3,5-di-n-alkylphenyl)phosphinomethyl)cyclobutane.

2. The process of claim 1 wherein the catalyst system comprises the rhodium complex and trans-1,2-bis(bis(3,5-di-methylphenyl)phosphinomethyl)-cyclobutane.

3. The process of claim 1 wherein the catalyst system comprises the rhodium complex and trans-1,2-bis(bis(3,5-di-ethylphenyl)phosphinomethyl)-cyclobutane.

4. The process of claim 1 wherein the solvent is selected from the group consisting of C$_5$-C$_{20}$ aliphatic hydrocarbons, C$_6$-C$_{12}$ aromatic hydrocarbons, ethers, alcohols, and mixtures thereof.

5. The process of claim 1 wherein the solvent is selected from the group consisting of toluene, cyclohexane, methyl t-butyl ether, and mixtures thereof.

6. The process of claim 1 wherein the rhodium complex comprises rhodium and ligands selected from the group consisting of hydride, carbonyl, trialkyl or triaryl phosphines, diphosphines, cyclopentadienyls, 2,4-alkanedionates, and mixtures thereof.

7. The process of claim 1 wherein the reaction is performed at a temperature within the range of about 45° C. to about 85° C. and a pressure within the range of about 30 to about 400 psig.

8. The process of claim 1 wherein the catalyst system further comprises a monophosphine compound.

9. The process of claim 8 wherein the monophosphine compound is triphenylphosphine.

10. The process of claim 1 further comprising hydrogenating the 4-hydroxybutyraldehyde in the presence of a hydrogenation catalyst to form 1,4-butanediol.

11. The process of claim 10 wherein the hydrogenation catalyst is a nickel catalyst.

* * * * *